(12) United States Patent
Leroy et al.

(10) Patent No.: US 10,022,111 B2
(45) Date of Patent: Jul. 17, 2018

(54) SURGICAL INSTRUMENT

(71) Applicant: Karl Storz SE & Co. KG, Tuttlingen (DE)

(72) Inventors: Joel Jules Louis Leroy, Bouvigny-Boyeffles (FR); Benjamin Rollet, Foix (FR); Sebastian Wagner, Bretten (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 485 days.

(21) Appl. No.: 13/673,584

(22) Filed: Nov. 9, 2012

(65) Prior Publication Data
US 2013/0123800 A1 May 16, 2013

(30) Foreign Application Priority Data

Nov. 11, 2011 (EP) .................................... 11188747

(51) Int. Cl.
*A61B 17/50* (2006.01)
*A61B 17/00* (2006.01)
*A61B 17/29* (2006.01)

(52) U.S. Cl.
CPC ........ *A61B 17/00234* (2013.01); *A61B 17/29* (2013.01); *A61B 2017/0046* (2013.01); *A61B 2017/00991* (2013.01); *A61B 2017/2901* (2013.01)

(58) Field of Classification Search
CPC . A61B 17/00; A61B 17/282; A61B 17/00234; A61B 17/29; A61B 2017/0046; A61B 2017/2901; A61B 2017/00991
See application file for complete search history.

(56) References Cited

U.S. PATENT DOCUMENTS

| | | | | |
|---|---|---|---|---|
| 5,370,659 A | * | 12/1994 | Sakashita | A61B 17/29 600/564 |
| 5,511,564 A | * | 4/1996 | Wilk | A61B 17/00234 128/898 |
| 5,527,339 A | * | 6/1996 | Koscher | A61B 17/29 606/205 |
| 5,582,617 A | | 12/1996 | Klieman et al. | |
| 5,792,165 A | * | 8/1998 | Klieman et al. | 606/170 |
| 5,849,022 A | * | 12/1998 | Sakashita | A61B 17/29 606/174 |

(Continued)

FOREIGN PATENT DOCUMENTS

DE 4324254 C1 1/1995

OTHER PUBLICATIONS

European Search Report Application No. EP 11 18 8747 Completed: Apr. 16, 2012 dated Apr. 24, 2012 5 pages.

*Primary Examiner* — Richard Louis
(74) *Attorney, Agent, or Firm* — Whitmyer IP Group LLC

(57) ABSTRACT

An endoscopic surgical instrument with an elongate shaft, a surgical tool arranged at a distal end of the shaft for conducting surgical manipulations and a handle arranged at a proximal end of the shaft for actuating the surgical tool. The shaft has an elongate shaft tube and an elongate actuation rod arranged movably within the shaft tube, the tool and the handle both being connected to the shaft tube and the actuating rod such that the tool can be actuated by the handle through a motion of the actuating rod relative to the shaft tube.

20 Claims, 17 Drawing Sheets

(56) References Cited

U.S. PATENT DOCUMENTS

| | | | | |
|---|---|---|---|---|
| 5,992,158 | A * | 11/1999 | Goddard | A61B 18/02 606/24 |
| 6,340,365 | B2 | 1/2002 | Dittrich et al. | |
| 2001/0037141 | A1* | 11/2001 | Yee | A61F 2/95 623/1.11 |
| 2005/0251144 | A1* | 11/2005 | Wilson et al. | 606/73 |
| 2007/0073247 | A1* | 3/2007 | Ewaschuk | A61B 17/29 604/264 |
| 2007/0213766 | A1* | 9/2007 | Ravikumar | A61B 90/50 606/205 |

* cited by examiner

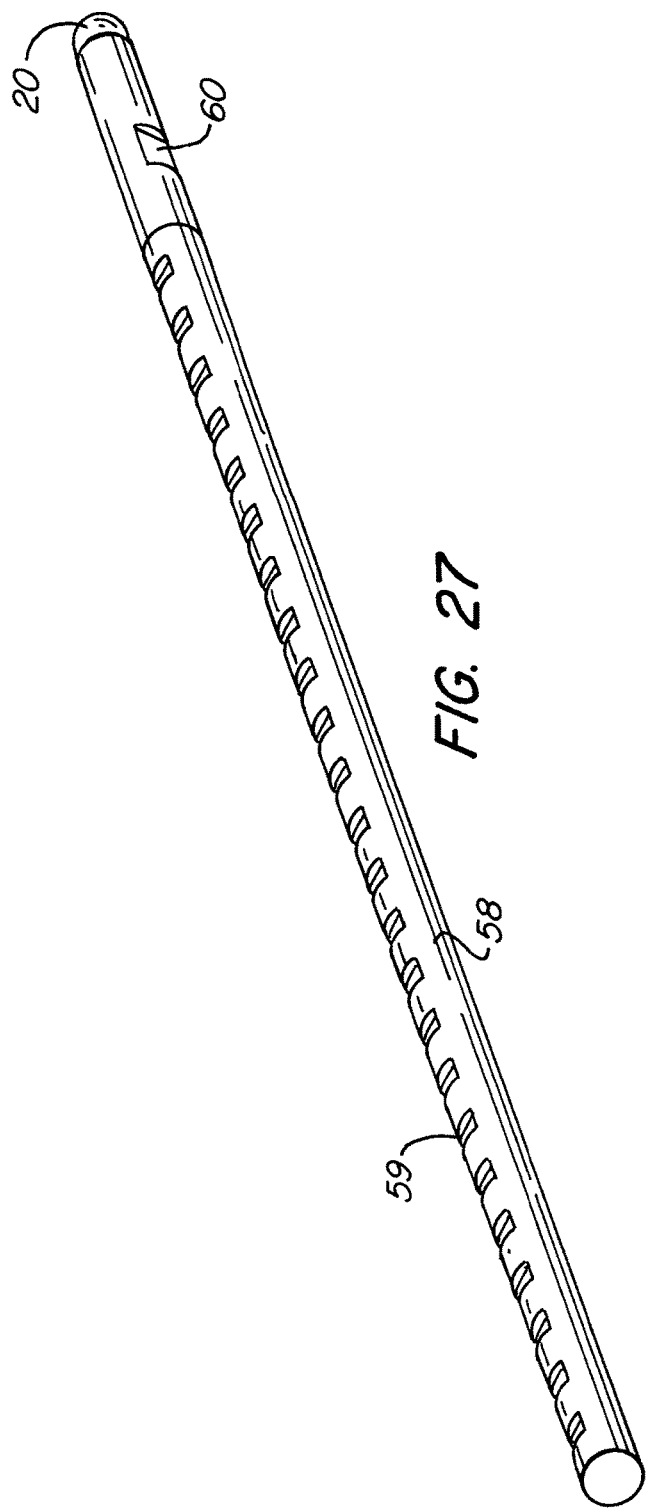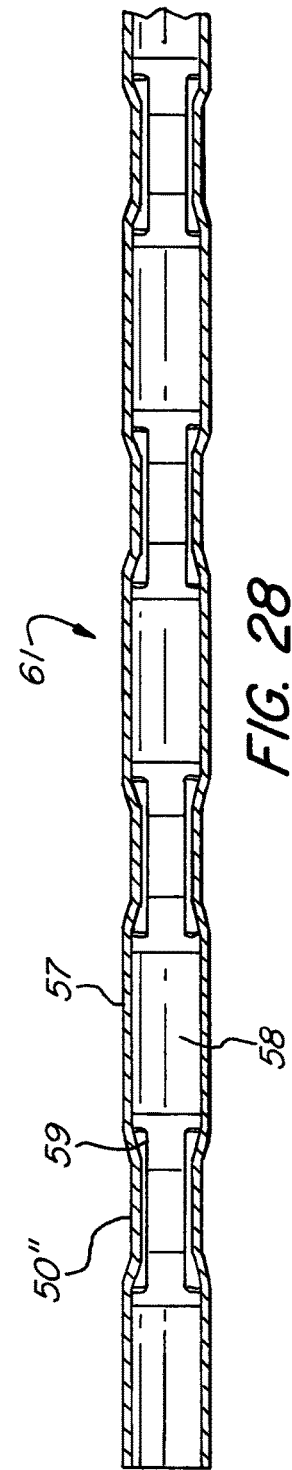

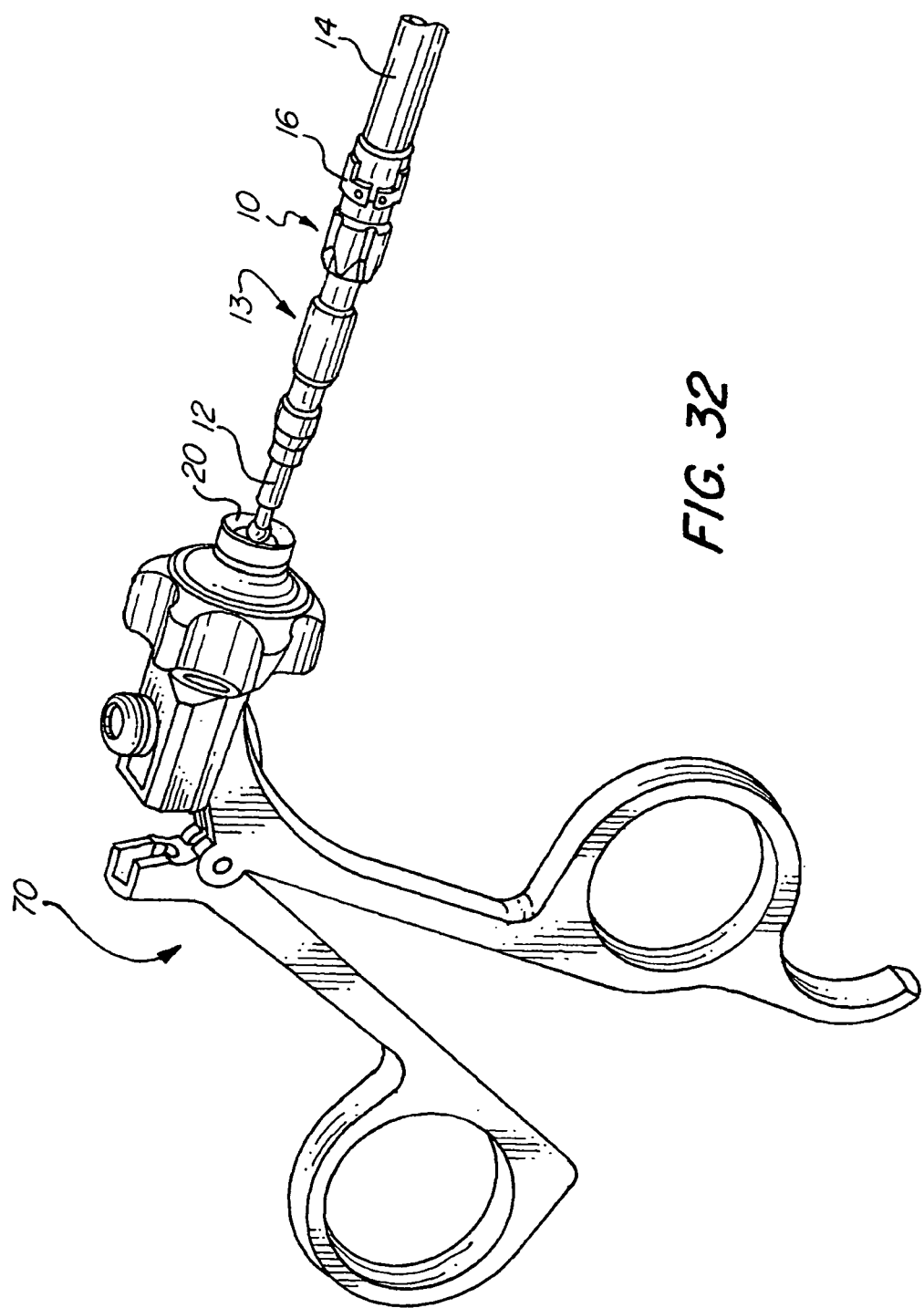

SURGICAL INSTRUMENT

FIELD OF THE INVENTION

The present invention relates to a surgical instrument, in particular to an endoscopic surgical instrument, comprising an elongate shaft, a surgical tool arranged at a distal end of the shaft for conducting surgical manipulations and a handle arranged at a proximal end of the shaft for actuating the surgical tool, wherein the elongate shaft comprises a shaft tube and an actuation rod arranged movably within the shaft tube and wherein the tool and the handle both are connected to the shaft tube and to the actuating rod such that the tool can be actuated by the handle through a motion of the actuating rod relative to the shaft tube.

BACKGROUND OF THE INVENTION

Instruments of this kind are known in the art. As disclosed, for example, in U.S. Pat. No. 6,340,365 B2, a medical instrument comprises a handle and a tubular shaft, within which a rod-shaped actuation element is held, which at its distal end carries two mouth parts. The shaft of the medical instrument is detachably connectable to the handle. For rotating the shaft and the mouth parts with respect to the handle, an adjusting wheel is provided.

In endoscopic surgery, in particular in laparoscopic surgery, surgical instruments frequently have considerable shaft lengths, in order to ensure that operating areas located at some distance from an endoscopic entry port can be reached. However, such a shaft length may result in an unfavorable working position for the surgeon in cases where the operating area is located close to the entry port. In order to alleviate this problem, in U.S. 2005/0033355 A1 a medical endoscopic instrument is disclosed wherein the handle can be secured on the instrument shaft so that it can be moved in an axial direction of the instrument shaft.

In some endoscopic surgical procedures, for example in transvaginal surgery of the gall bladder, an even longer shaft may be required, for example up to a length of about 70 cm. Such surgical procedures, in which the entry port is at a considerable distance from the organ to be accessed, have become increasingly widespread for aesthetic as well as for medical reasons. In particular, a visible scar can be avoided if the incision required for introducing surgical instruments is made near the navel or through a natural orifice. An instrument of the length frequently required in such procedures, however, would be too long to fit into standard sterilization trays. Moreover, such an instrument would be disadvantageous if the operating area is closer to the entry port.

SUMMARY OF THE INVENTION

It is therefore an object of the present invention to provide a surgical instrument, in particular an endoscopic surgical instrument, that avoids the disadvantages mentioned. In particular, it is an object of the present invention to provide a surgical instrument which is useable in a larger variety of surgical situations, including situations with a long distance between the operating area and the endoscopic entry port and situations with a shorter distance between the operating area and the entry port, preferably without exceeding the capacity of standard sterilization equipment.

This object is met by a surgical instrument according to the present teachings. Preferred embodiments of the invention are also disclosed.

According to one embodiment of the present invention, a surgical instrument, in particular an endoscopic surgical instrument, comprises an elongate shaft for insertion into a body cavity. Such insertion usually is effected through an endoscopic entry port, which may be artificially created by an incision or may be a natural orifice of the body. An entry port may also be formed by an incision within a natural orifice. The surgical instrument further comprises a surgical tool for conducting surgical manipulations such as cutting, holding, retracting or the like. The tool is arranged at a distal end of the shaft, i.e. at that end of the shaft that is more distant from the surgeon when the instrument is in use, in order to be introduced into the body cavity with the shaft. The surgical instrument also comprises a handle, which is arranged at a proximal end of the shaft, i.e. at that end of the shaft being closer to the surgeon, and is designed for actuating the surgical tool.

The elongate shaft may comprise an elongate shaft tube and an elongate actuation rod arranged movably within the shaft tube. In particular, the actuation rod may be slidably guided within the shaft tube. The tool and the handle both are connected to the shaft tube and to the actuation rod in such a manner that the tool can be actuated by the handle by means of a motion of the actuation rod relative to the shaft tube. To this end, connecting means or coupling elements are provided for connecting the tool to the distal ends of the shaft tube and to the actuation rod. For example, a grasping tool comprising two cooperating jaw elements may be connected to the shaft tube and to the actuation rod in such a manner that a fixed jaw element is rigidly connected to the shaft tube, while a movable jaw element is pivotably connected to the shaft tube and by means of a lever mechanism to the distal end of the actuation rod. The handle may be connected or connectable to the proximal ends of the shaft tube and the actuation rod, for example, a fixed handle element may be rigidly or rotatably connectable to the shaft tube and a movable handle element may be connectable to the actuation rod. In this way, operating the movable handle element with respect to the fixed handle element results in a longitudinal displacement of the actuation rod with respect to the shaft tube, thus effecting a motion of the movable jaw element with respect to the fixed jaw element. The tool may comprise two counter-acting movable jaw elements, a multiplicity of jaw elements, or other kinds of tool elements, such as cutting, punching, or suturing elements, for example, which may involve a longitudinal motion. The handle may include more than one movable handle element and/or a handle element operated by a longitudinal shift. In principle, the instrument may also be operated by a rotation of a handle element and/or the actuation rod and/or a tool element with respect to a longitudinal axis of the shaft tube. Preferably, the surgical instrument is a rigid instrument, the shaft being substantially rigid. The instrument may be designed for direct insertion through an incision or another kind of entry port, or for insertion through a trocar or through an instrument channel of an endoscope, for example. In particular, the instrument may be designed for single port endoscopic surgery.

According to one embodiment of the present invention, both of the shaft tube and the actuation rod are telescopically adjustable to a multiplicity of lengths of the shaft tube and the actuation rod, respectively, and lockable at the respective lengths. In particular, the shaft tube comprises an elongate outer shaft tube and an elongate inner shaft tube, the outer shaft tube being displaceable in a longitudinal direction along the inner shaft tube, and the outer shaft tube being lockable with respect to the inner shaft tube in a multiplicity of longitudinal positions. In particular, the inner shaft tube is arranged co-axially and at least partly within the outer shaft tube and is slideably guided within the outer shaft tube, i.e., the outer shaft tube can be slid over the inner shaft tube. For locking the outer shaft tube with respect to the inner shaft tube, the outer and/or inner shaft tube may be equipped with locking means. In a contracted position, the inner shaft tube may longitudinally substantially coincide with the outer shaft tube, while in an extended position, the inner shaft tube may protrude by a substantial part of its length over the outer shaft tube into a distal or a proximal direction.

Moreover, the actuation rod may comprise an actuation rod tube and an actuation rod core. The actuation rod core is arranged at least partially within the actuation rod tube, preferably coaxially with the actuation rod tube. The actuation rod tube is displaceable in a longitudinal direction relative to the actuation rod core and can be locked with respect to the actuation rod core in a multiplicity of longitudinal positions which correspond to the longitudinal positions of the outer shaft tube and the inner shaft tube. In a similar manner as described in relation to the inner and outer shaft tubes, the actuation rod core can substantially fill the inner volume of the actuation rod tube in a contracted position, while it protrudes beyond the actuation rod tube to the distal or proximal direction in an extended position. The length of the shaft tube fixed by locking the outer and inner shaft tubes with respect to each other corresponds to the length of the actuation rod fixed by locking the actuation rod tube and the actuation rod core with respect to each other such that the instrument is operable at the corresponding shaft length, i.e. in particular, the lengths of the shaft tube and the actuation rod are substantially the same.

In this way, the surgical instrument is simply and reliably adjustable to a multiplicity of lengths. Thus, for example, in a transvaginal gall bladder operation a maximal length of the surgical instrument can be chosen, while in another laparoscopic intervention, the instrument can be employed at a reduced length. In this way, the total length of the surgical instrument and in particular the distance between the surgical tool and the handle are adjustable according to the requirements of a large variety of surgical situations in a simple manner. The instrument length may even be adjustable during an endoscopic intervention. At least with a reduced length chosen, the instrument may be small enough to fit into standard sterilization equipment.

According to a preferred embodiment of the invention, the outer shaft tube is lockable with respect to the inner shaft tube by a bayonet-type lock. Such a bayonet-type lock may comprise, in particular, a first bayonet element arranged on the outside of the inner shaft tube and a second bayonet element arranged on the inside of the outer shaft tube. The first and second bayonet elements co-operate such that in at least one first rotational position of the inner shaft tube relative to the outer shaft tube, the inner shaft tube is freely movable in the longitudinal direction relative to the outer shaft tube, while in at least one second rotational position, the inner shaft tube is locked against longitudinal motion within the outer shaft tube. This means that for adjusting the length of the shaft tube, the inner shaft tube is rotated into the first position, moved to a desired longitudinal position in which the shaft tube has a desired total length, and then rotated into the second rotational position and thus locked against longitudinal displacement. The bayonet-type lock is designed to permit locking in a multiplicity of longitudinal positions of the inner shaft tube relative to the outer shaft tube. In particular, the inner shaft tube may exhibit a multiplicity of first bayonet elements and/or the outer shaft tube may exhibit a multiplicity of second bayonet elements being placed at a distance to each other so that locking in positions at the respective distances is enabled. Additionally or alternatively, the first and second bayonet elements may be designed for locking in a multiplicity of longitudinal positions. A bayonet-type lock is a simple and reliable means for effective locking against relative longitudinal displacement of the inner and outer shaft tubes and thus for locking the shaft tube at a desired length.

Preferably, the bayonet-type lock is a threaded bayonet lock. In particular, the thread may have non-zero pitch, the first and second bayonet elements forming a longitudinally grooved screw and nut, respectively. Alternatively, the thread may have zero pitch, the first and second bayonet elements exhibiting a multiplicity of parallel grooves and ridges in a circumferential direction of the inner and outer shaft tubes. In this way, locking in a large number of longitudinal positions can be accomplished.

In order to secure the bayonet-type lock against unlocking, preferably a blocking element is provided that exhibits an elongate shape and can be introduced into a hollow space between the outer and the inner shaft tubes that remains after rotating the inner shaft tube relative to the outer shaft tube into a locking position. For unlocking, the blocking element has to be removed. Preferably, the blocking element is introducible from a proximal end of the instrument. In this way, a particularly safe operation of the instrument is achievable in a simple and effective manner.

According to a further preferred embodiment, the outer shaft tube comprises a proximal and a distal section, the proximal section comprising first ratchet means co-operating with the inner tube to permit relative motion of the proximal section only into a distal direction of the inner shaft tube, and the distal section comprising second ratchet means for permitting a motion of the distal section relative to the inner shaft tube only in a proximal direction. Thus, by sliding, for example, the proximal section over the inner tube into a desired longitudinal position and counter-locking the proximal section by moving the distal section until it contacts the proximal section, the outer shaft tube can be locked in a particular longitudinal position with respect to the inner tube. The ratchet means may consist of at least one detent element, co-operating with a rack arranged in a longitudinal direction along an outer surface of the inner shaft tube, the rack preferably comprising asymmetrical teeth. Alternatively, the ratchet means may consist of a detent element connected to the inner shaft tube co-operating with a toothed rack fixed on an inner surface along a longitudinal direction of the outer shaft tube. In this way, a quick adjustment and safe locking of the outer and inner shaft tubes relative to each other is achievable.

Preferably, a proximal end of the distal section and a distal end of the proximal section are formed in an interlocking manner such that the proximal and the distal sections can be rotationally locked with each other. In this way, the proximal and distal sections of the outer shaft tube form a unit when locked.

Still preferably, the inner and outer shaft tubes are rotatable with respect to each other for releasing the lock. In particular, by a rotational motion of the inner tube relative to the outer tube, at least one detent element may be disengaged from the rack, such that a free longitudinal translational movement of the inner shaft tube in the outer shaft tube is permitted. The detent element may act upon a circumferentially flattened portion forming part of the rack with which it co-operates, such that a mechanical resistance must be overcome in the rotational movement for unlocking the shaft tubes. Additionally or alternatively, the inner shaft tube may comprise a flattened section co-operating with a corresponding flattened section of the outer shaft tube. In this way, a simple operation for locking and unlocking the inner and outer shaft tubes can be facilitated. The unlocking by rotation of the inner shaft tube with respect to the outer shaft tube can be inhibited by a cover tube enclosing the outer tube.

According to a further preferred embodiment, the outer shaft tube is connected or connectable to a clamping ring, the clamping ring enclosing the inner shaft tube and being movable along the inner shaft tube in a longitudinal direction. The clamping ring may form part of the outer shaft tube or may be a separate element. The clamping ring comprises non-parallel outer and inner cylindrical surfaces such that it frictionally engages with the inner tube when its outer cylindrical surface is biased into an orientation that is coaxial with the inner shaft tube. A force for effecting such a bias can be exerted in particular by a cover tube enclosing the outer shaft tube and the clamping ring. Due to the outer shaft tube being connected or connectable to the clamping ring, the outer shaft tube can thus be locked longitudinally with respect to the inner shaft tube. As the outer surface of the inner shaft tube in this embodiment may be substantially cylindrical without any particular locking means, the outer shaft tube can be locked in this way at substantially any desired relative longitudinal position along the inner shaft tube without being confined to particular pre-determined positions. In this way, the shaft may be adjustable to substantially any length within a permissible range.

Preferably, the clamping ring is connected to an end section of the outer tube by tooth means, at least one tooth of the clamping ring co-operating with at least one indentation of the end section of the outer shaft tube, or vice versa. The tooth means and the indentation extend into a circumferential direction of the clamping ring and the outer shaft tube and advantageously have a height or depth respectively, such that the tooth means cannot be disengaged from the indentation as long as the cover tube is in place. In this way, a safe and particularly versatile embodiment is achievable.

According to a further preferred embodiment, the outer shaft tube comprises at least one clamping element being held movably on or within the outer shaft tube. The inner shaft tube comprises at least one window or recess for engaging with the clamping element. Preferably, the clamping element is resiliently biased towards the inner tube, being held in a position extending to the inside beyond the inner surface of the outer shaft tube, thus engaging the at least one window or recess when it coincides with the clamping element. In this way, the outer shaft tube can be locked with the inner shaft tube. Additionally or alternatively, the clamping element may be pressed into and held in the window or recess by a cover tube enclosing the outer tube. Preferably, the thickness of the clamping element exceeds a thickness of a wall of the outer tube, being firmly held in the window or recess of the inner shaft tube by the cover tube. In this way, an effective blocking of the outer and inner tubes with respect to each other can be achieved.

Alternatively, the inner shaft tube may exhibit at least one clamping element being held movably, preferably resiliently, on or within the inner shaft tube. The outer shaft tube comprises at least one window or recess for engaging with the clamping element. Thus, in a similar way as described above, locking of the outer shaft tube with respect to the inner shaft tube can be achieved. An effective blocking of the outer and inner shaft tubes relative to each other can be achieved by the actuation rod being introduced into the inner shaft tube if the thickness of the clamping element exceeds a thickness of a wall of the inner shaft tube.

In each case, at least one clamping element and a multiplicity of windows or recesses, or vice versa, is provided, the multiplicity of clamping elements or windows or recesses, respectively, being placed at a longitudinal distance from each other for enabling locking in a multiplicity of longitudinal positions. Preferably, a multiplicity of clamping elements and a multiplicity of windows or recesses are provided such that in any permitted elongation a multiplicity of clamping elements engage with a multiplicity of windows or recesses, thus providing a most stable lock.

While the above described embodiments have been described in relation to the shaft tube, the length of the actuation rod may be adjusted in a similar way. In particular, the actuation rod may comprise an actuation rod tube and actuation rod core designed for longitudinal motion and locking with respect to each other in a similar way as the outer shaft tube and the inner shaft tube. Alternatively, the actuation rod tube and actuation rod core may be designed for relative longitudinal motion and locking in a different way than the outer shaft tube and the inner shaft tube. Thus, for example, the outer shaft tube and the inner shaft tube may be lockable by a bayonet-type lock, while the actuation rod tube and actuation rod core may be movable and lockable by a ratchet mechanism, by a clamping ring being blockable by the inner shaft tube, or by clamping elements engaging with windows or recesses, the respective locking mechanisms having been described above. Moreover, the outer shaft tube and the inner shaft tube may be lockable by a ratchet mechanism and the actuation rod tube and actuation rod core may be movable and lockable by a bayonet-type lock, by a clamping ring being blockable by the inner shaft tube, or by clamping elements engaging with windows or recesses, the respective locking mechanisms being as described above. The outer shaft tube and the inner shaft tube may also be lockable by a clamping ring, while the actuation rod tube and actuation rod core may be movable and lockable by a bayonet-type lock, by a ratchet mechanism, or by clamping elements engaging with windows or recesses, the respective locking mechanisms being as described above. The outer shaft tube and the inner shaft tube may also be lockable by clamping elements engaging with windows or recesses, and the actuation rod tube and actuation rod core may be movable and lockable by a bayonet-type lock, by a ratchet mechanism, or by a clamping ring being blockable by the inner shaft tube, all locking mechanisms mentioned having been described above.

The inner shaft tube may be connected to the handle of the surgical instrument and the outer shaft tube may be connected to the surgical tool, the inner shaft tube being movable with respect to the outer shaft tube to protrude in a proximal direction from the outer shaft tube for extending the length of the shaft. Alternatively, the inner shaft tube may be connected to the tool of the surgical instrument and the outer shaft tube may be connected to the handle, the inner shaft tube being movable with respect to the outer shaft tube to protrude in a distal direction for extending the length of the shaft. The inner and outer shafts may be enclosed by a cover tube and, possibly, an additional outer sheath for protecting the inner and outer shaft tubes against the intrusion of body fluids, for providing a smooth outer surface to facilitate insertion and removal of the instrument, and/or for blocking the outer and inner shaft tubes in the desired relative longitudinal position and thus fixing the shaft at the desired length. The cover tube may fit the outer surface of the outer shaft tube tightly to accomplish the latter object.

In a similar way, the actuation rod core may be connected to the handle and the actuation rod tube to the tool, or vice versa. The actuation rod may fit tightly but movably in the inner shaft tube, such that the actuation rod and/or the shaft is blocked safely at a desired length.

Most preferably, the surgical instrument can be disassembled for cleaning and sterilization. In particular, the handle may be detachable from the shaft. When the shaft has been disassembled, it can be re-assembled at a desired length, thus adjusting its length to a length which is optimal for a particular operation or surgical situation. Preferably, the shaft can be adjusted to another length during the surgical intervention.

In order to ensure a sufficient bending stiffness, there may be a minimal longitudinal overlap of the inner and outer shaft tubes required. The means employed in the various embodiments for locking the inner and outer shaft tubes relative to each other can be arranged along the inner and outer tubes correspondingly to ensure at least the required overlap.

The features of the invention as mentioned above and as described below apply not only in the combinations mentioned but also in other combinations or alone, without leaving the scope of the present invention.

BRIEF DESCRIPTION OF THE DRAWINGS

Further aspects of the present invention will be apparent from the figures and from the description of the particular embodiments that follows.

FIG. 27 shows the actuation rod core according to the fourth embodiment in a perspective view;

FIG. 28 shows the actuation rod according to FIGS. 26 and 27 in an assembled state in a longitudinal sectional view;

FIG. 32 shows the proximal end of the surgical instrument, including a handle.

DETAILED DESCRIPTION OF THE INVENTION

Figure 1:
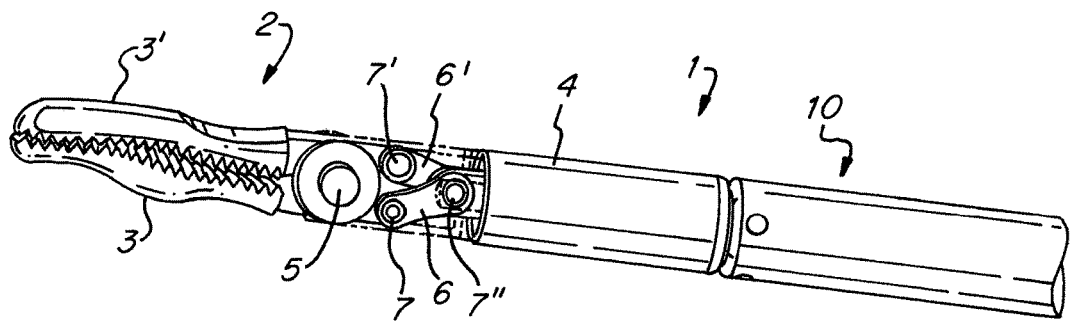
FIG. 1 shows a distal end portion of an endoscopic surgical instrument in an assembled state in a perspective view.

According to an embodiment of the invention and as shown in FIG. 1, an endoscopic surgical instrument 1 comprises a surgical tool 2 and an elongate shaft 10. The surgical tool may comprise two jaw elements 3, 3' cooperating with each other for grasping tissue, for example. The jaw elements 3, 3' are pivotably mounted to a tool base 4 by a hinge 5. The jaw elements 3, 3' are connected by articulating levers 6, 6' comprising joints 7, 7', 7" to a proximal end portion of a push/pull rod (not visible in FIG. 1).

Figure 2:
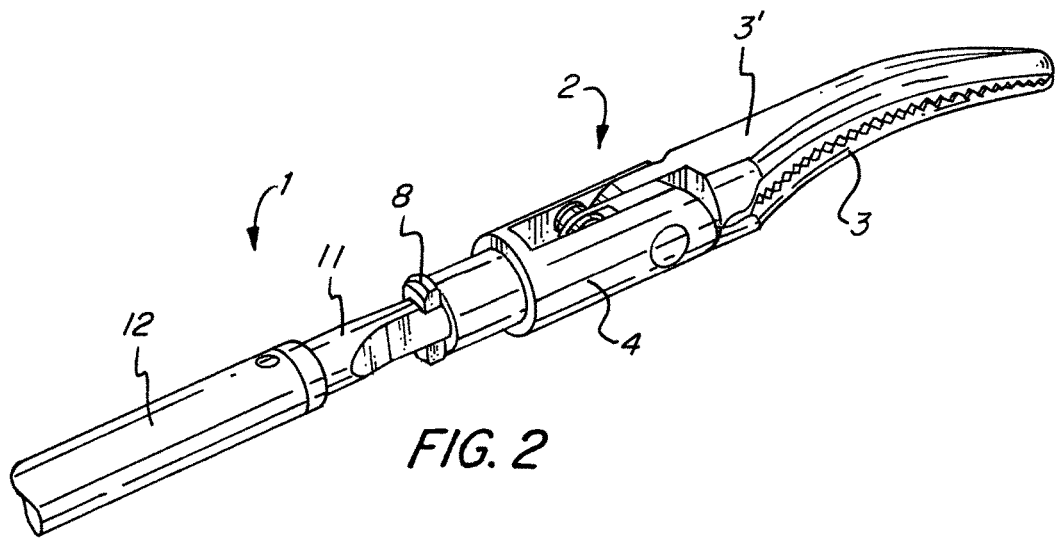
FIG. 2 shows a distal end portion of an endoscopic surgical instrument in a partly disassembled state in a perspective view.

According to FIG. 2, in a particular embodiment, the tool 2 comprises two counteracting jaw elements 3, 3' pivotably mounted on a tool base 4 comprising a bayonet element 8 slidingly movable on a distal end section 11 of a push/pull rod 12. The jaw elements 3, 3' are connected by articulating levers to the end section 11. The bayonet element 8 can be locked with an end section of a shaft tube (not shown in FIG. 2). In FIG. 2, a shaft tube to be slid over the push/pull rod 12 and connected to the tool base 4 via the bayonet element 8 has been removed.

Figure 3:
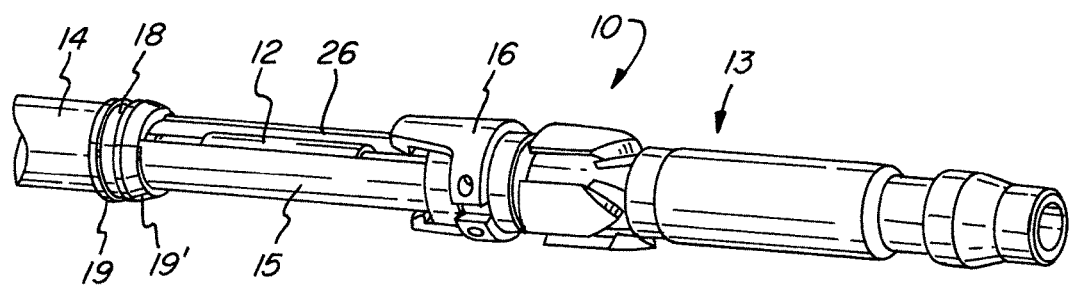
FIG. 3 shows the proximal end section of an endoscope shaft with a cover tube removed in a perspective view.

As shown in FIG. 3, the proximal end section of an endoscope shaft 10, according to an embodiment of the invention, comprises a coupling mechanism 13 for coupling the endoscope shaft 10 to a handle (70, shown in FIG. 32). The coupling mechanism 13 and the handle may be designed as disclosed in U.S. Pat. No. 6,340,365 B2, which is herewith included by reference. In the situation depicted in FIG. 3, an outer shaft tube 14 almost completely encloses an inner shaft tube 15. For illustrative purposes, in FIG. 3 the inner shaft tube 15 is shown cut open, making the push/pull rod 12 partly visible. Although in FIG. 3 a blocking rod 26 is symbolically indicated forming part of a first embodiment of the invention (see below), other features indicated in FIG. 3, in particular the design of the coupling mechanism 13, may apply to other embodiments as well.

Figure 4:
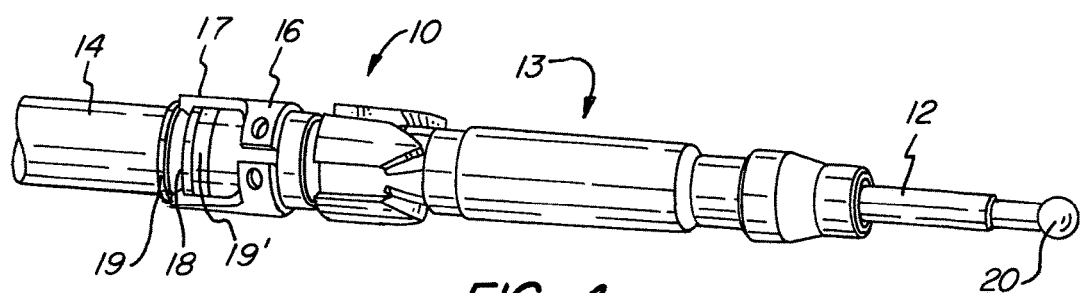
FIG. 4 shows the proximal end section of an endoscope shaft as shown in FIG. 3, but with the outer shaft tube completely slid over the inner shaft tube.

During assembly of the endoscopic surgical instrument 1, the outer shaft tube 14 is shifted towards the proximal end of the shaft, i.e. towards the coupling mechanism 13. In its assembled state, which is shown in FIG. 4, the outer shaft rube 14 abuts the coupling mechanism 13, being held to the proximal section of the shaft and the coupling mechanism by a circular dip 16, which includes resilient detent means 17 fitting into a circumferential groove 18 formed between two rings 19, 19' fixed near the proximal end of the outer shaft tube 14. The dip 16 comprises an open ring-shaped section by which the clip 16 is mountable on the proximal end of the shaft tube. In the final slate, the detent means 17 are held into the groove 18 by a cover tube placed over the circular clip 16. As shown in FIG. 4, the proximal end section of the push/pull rod 12 protrudes from the proximal end section of the shaft tube and the coupling mechanism 13. The proximal end section of the push/pull rod 12 exhibits a ball 20 to be engaged by a movable hand piece of the handle (70, shown in FIG. 32). In FIGS. 3 and 4 a cover tube to be slid over the outer shaft tube 14 and the clip 16, thereby holding the clip 16 compressed, is not shown.

Figure 5:
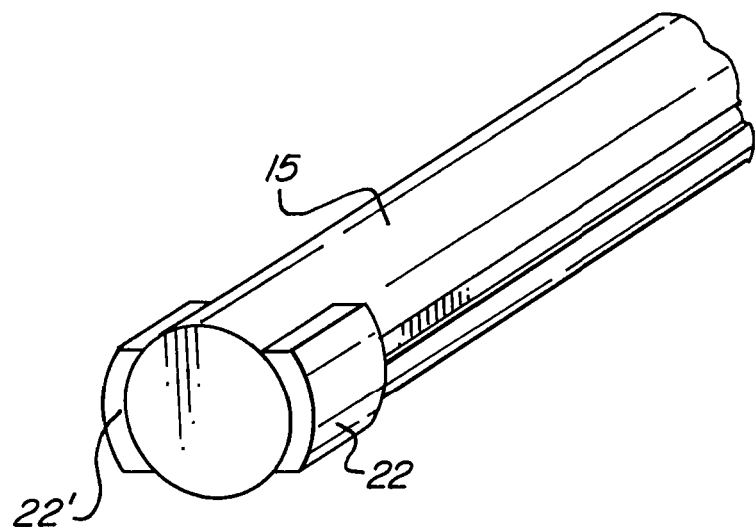
FIG. 5 shows an inner shaft tube according to a first embodiment of the invention in a perspective view.
Figure 6:
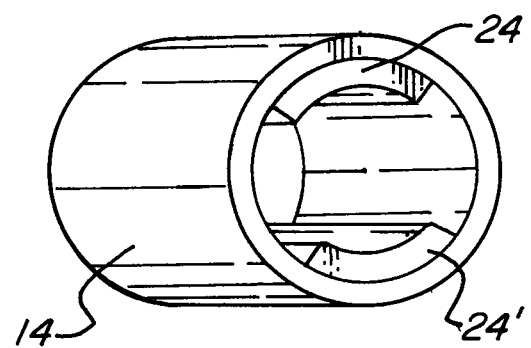
FIG. 6 shows an outer shaft tube according to the embodiment of FIG. 5 in a perspective view.

According to a first embodiment of the invention, an inner shaft tube 15 exhibits first bayonet elements 22, 22' close to one of its ends (see FIG. 5). As shown in FIG. 6, an outer shaft tube 14, only a section of which is shown in FIG. 6, has second bayonet elements 24, 24' cooperating with the first bayonet elements 22, 22'. In particular, the first and second bayonet elements 22, 22', 24, 24' may exhibit corresponding threads or circumferential grooves and ridges (not shown in FIGS. 5 and 6). The first and second bayonet elements 22, 22', 24, 24' each extend over approximately 90° as seen from a longitudinal axis of the outer and inner shaft tubes 14, 15. The inner shaft tube 15 includes a cavity extending longitudinally for housing the actuating rod (not shown in FIG. 5).

Figure 7:
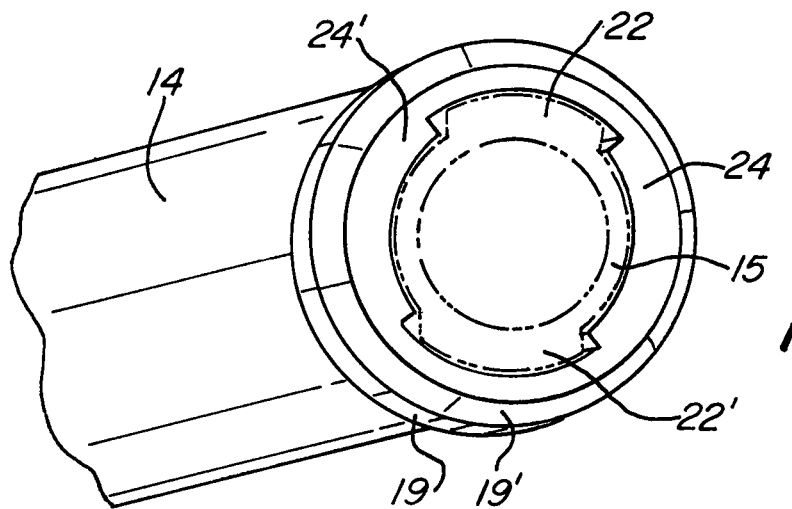
FIG. 7 shows the inner shaft tube of FIG. 5 accommodated within the outer shaft tube of FIG. 6 in a perspective view.
Figure 8:
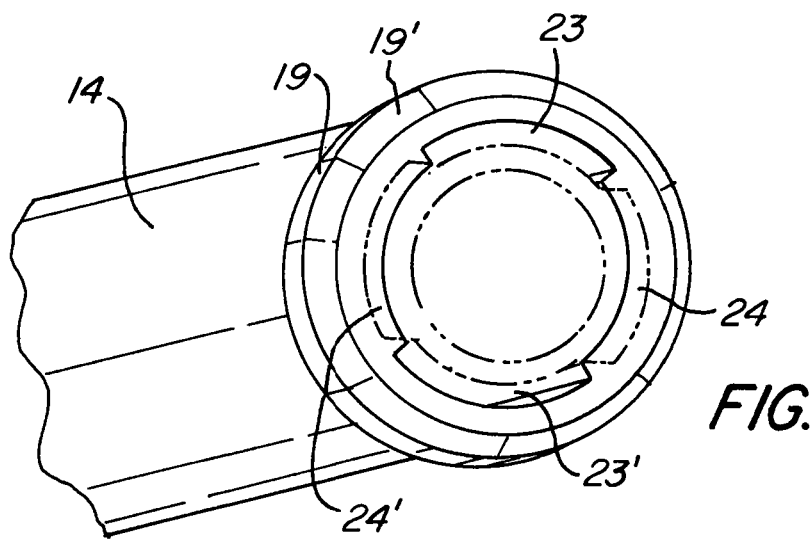
FIG. 8 shows the inner and outer shaft tubes as shown in FIG. 7 in the locked position, in a perspective view.

For adjusting the shaft tube to a desired length, the inner shaft tube 15 is turned into a rotational position in which the first bayonet elements 22, 22' fit between the second bayonet means 24, 24'. The inner shaft tube 15 is then slidingly moved into the desired longitudinal position, which may be, for example, the fully contracted position, in which the inner shaft tube longitudinally substantially coincides with the outer shaft tube 14 (FIG. 7). In the next step as shown in FIG. 8, the inner shaft tube 15 is rotated with respect to the outer shaft tube 14, such that the first and second bayonet elements 22, 22', 24, 24' engage with each other, the outer and inner shaft tubes 14, 15 being locked longitudinally with respect to each other. Finally, a blocking element 25 is introduced from a proximal end of the shaft such that blocking rods fill the hollow spaces 23, 23' between the second bayonet elements 24, 24', which in the locked position are no longer filled by the first bayonet elements 22, 22' (see FIG. 8). The coaxial rings 19, 19' forming a groove for engagement by the detent means 17 of the circular clip 16 are also visible in FIGS. 7 and 8.

Figure 9:
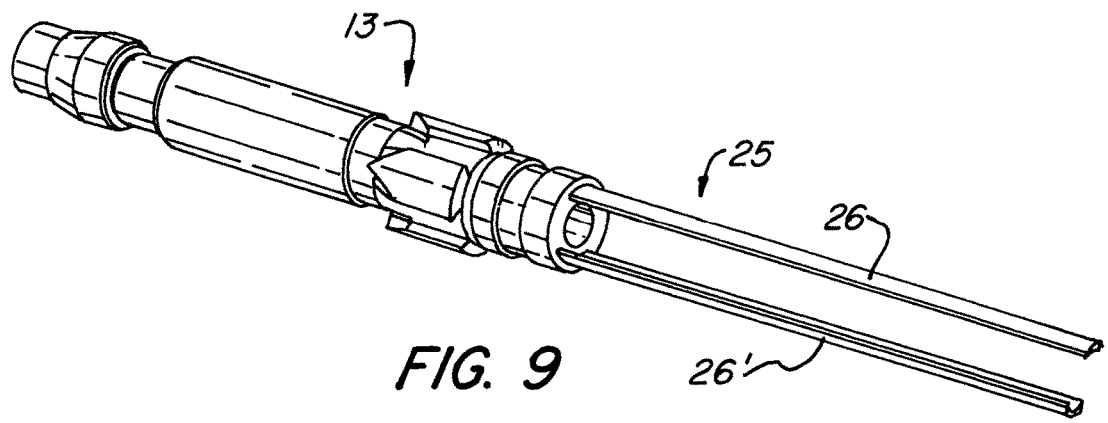
FIG. 9 shows a blocking element connected to the coupling mechanism, according to the first embodiment of the invention, in a side perspective view.
Figure 10:
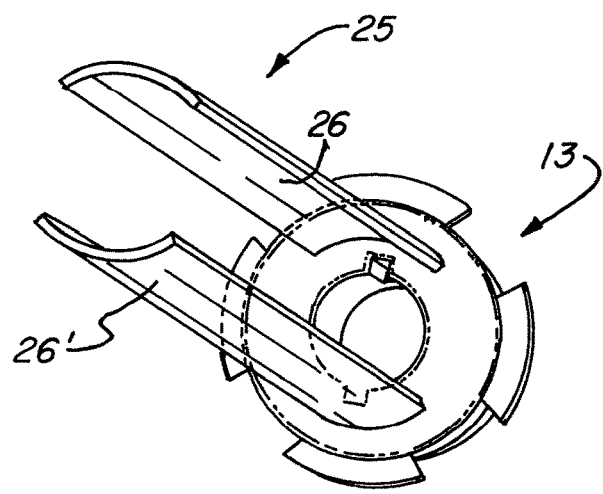
FIG. 10 shows a blocking element of FIG. 9 in a front perspective view.

The blocking element 25 is shown in FIG. 9 attached to the coupling mechanism 13. In FIG. 10 the blocking element 25 with the blocking rods 26, 26' is depicted in a perspective view from a distal direction. It is to be noted that the blocking rods 26, 26' need not be particularly stiff in order to fulfill their purpose of securing the bayonet lock against unlocking. This is due to the fact that the blocking rods 26, 26' only need to fill the hollow spaces 23, 23', while rotational stiffness is provided by the inner and outer shaft tubes 15, 14.

Figure 11:
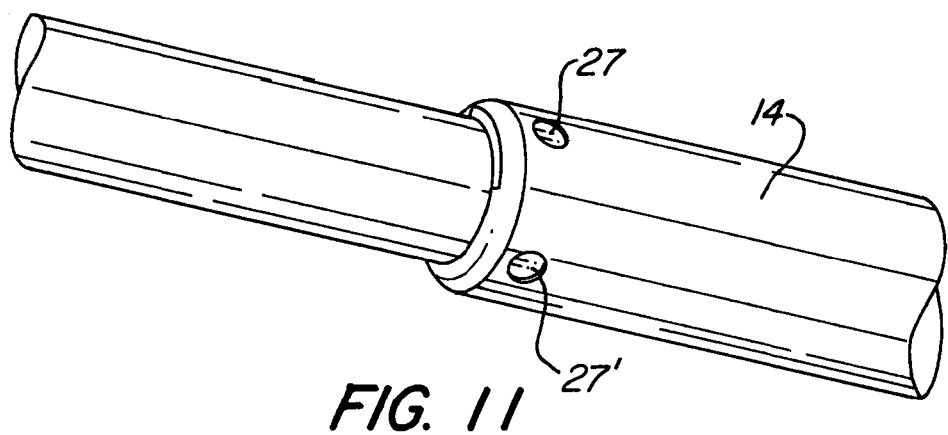
FIG. 11 shows the distal end section of a shaft tube according to the first embodiment, with an outer cover of the tool base removed.

As indicated in FIG. 11, a distal section of the outer shaft tube 14 and, possibly, a cover tube and an outer sheath may exhibit one or several windows 27, 27', through which the locking position of the inner shaft tube 15 can be discerned from the outside. For this purpose, for example, the inner shaft tube 15 may be marked with a colour as an indicator of the correct rotational orientation.

Figure 12:
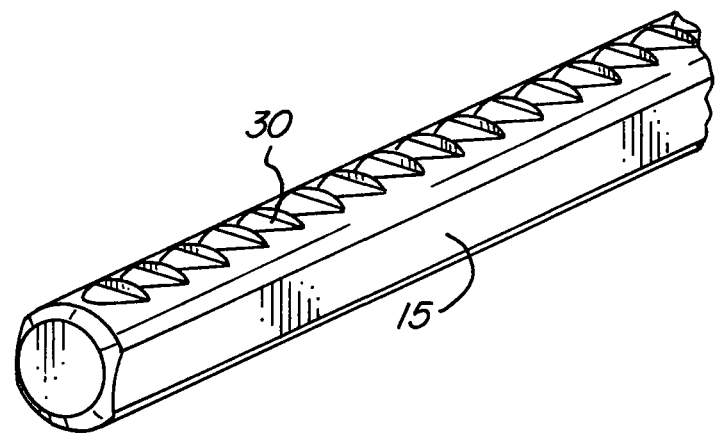
FIG. 12 shows the inner shaft tube according to a second embodiment of the invention in a perspective view.
Figure 13:
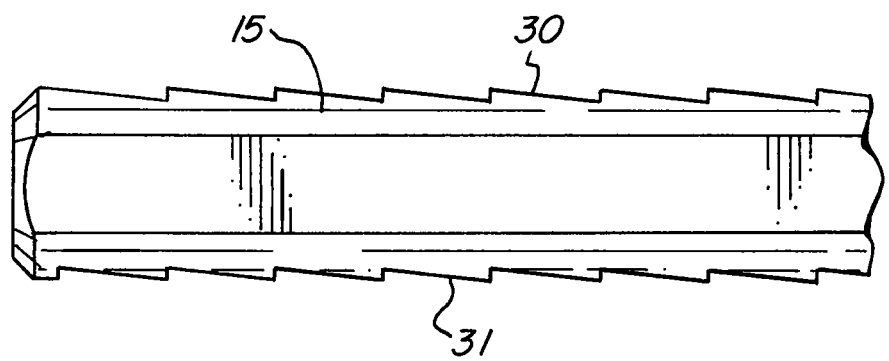
FIG. 13 shows the inner shaft tube of FIG. 12 in a longitudinal sectional view.
Figure 14:
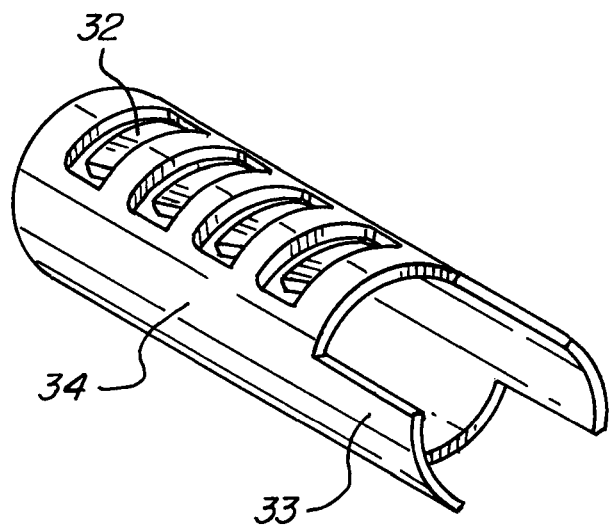
FIG. 14 shows the proximal section of the outer shaft tube according to the second embodiment of the invention.
Figure 15:
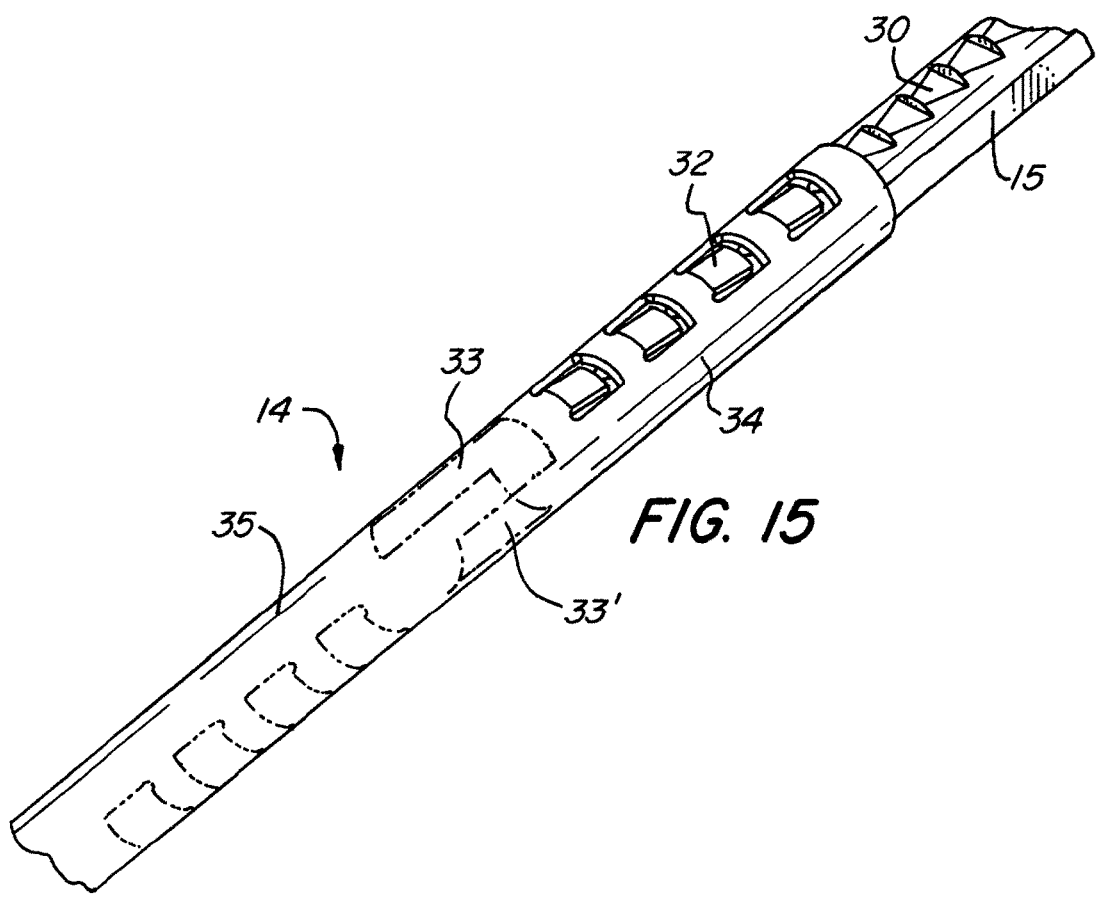
FIG. 15 shows the proximal and distal sections of the outer shaft tube being locked against each other on the inner shaft tube, according to the second embodiment.

According to a second embodiment, as shown in FIGS. 12 and 13, the inner shaft tube 15 at opposing sides exhibits asymmetrical racks 30, 31. The outer shaft tube consists of a proximal and a distal section, each of which on one side exhibits spring shackles 32 bent to the inside, and an interlocking end 33, the proximal section 34 of the outer shaft tube being shown in FIG. 14. The proximal section 34 and the distal section 35 of the outer shaft tube may be of different lengths, the distal section 33 having a longer length, for example, and the proximal 34 section being designed as a locking cap. As shown in FIG. 15, the proximal section 34 and the distal section 35, having been slid over the inner shaft tube 15 from opposing directions with the spring shackles 32 co-operating with the opposing racks 30, 31 of the inner shaft tube 15, are locked against each other and are connected by their inter-locking ends 33, 33'. For releasing the lock, the outer shaft tube 14 formed by the proximal and distal sections 34, 35 is rotated with respect to the inner shaft tube, releasing the spring shackles 32 from the racks 30, 31 and thus enabling shifting the proximal and distal sections 34, 35 along the inner shaft tube 15. The inner shaft tube 15 may comprise flattened sections co-operating with flattened sections on the inner surface of the outer shaft tube 14 such that a pre-determined angular momentum must be exerted to accomplish rotation of the inner shaft tube 15 relative to the outer shaft tube 14. The rotation may be blocked by a cover tube slid over the outer shaft tube 14.

Figure 16:
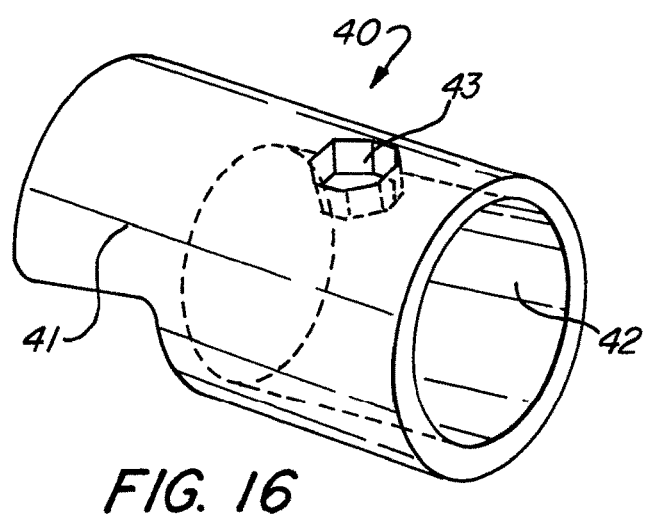
FIG. 16 shows an over-center ring employed in a third embodiment of the invention.
Figure 17:
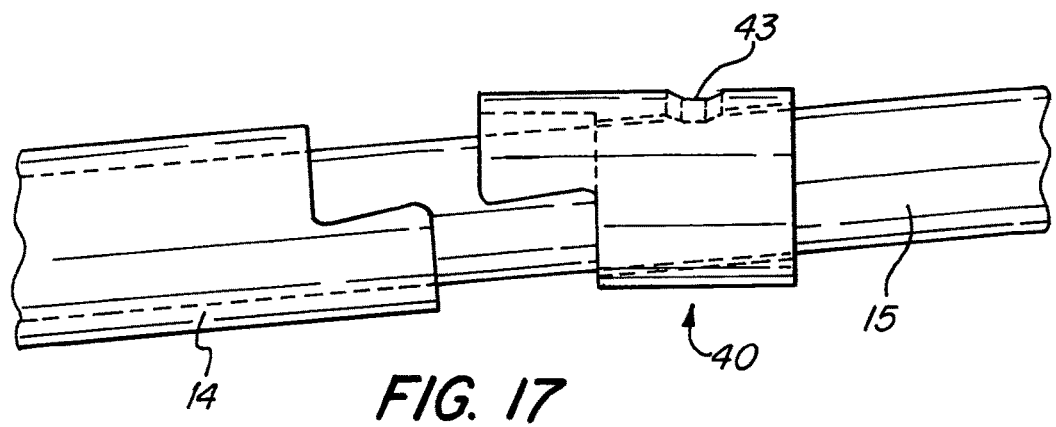
FIG. 17 shows the over-center ring of FIG. 16 being slid over the inner shaft tube.
Figure 18:
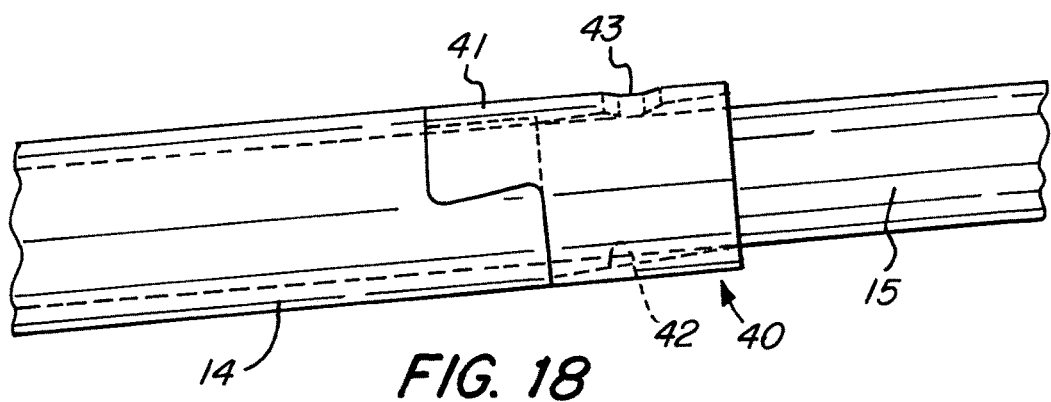
FIG. 18 shows the over-center ring of FIG. 16 in locked orientation.

According to a third embodiment of the invention, a clamping ring is employed for locking the outer shaft tube on the inner shaft tube. The clamping ring is an over-center ring 40, which has approximately cylindrical outer and inner surfaces 41, 42, with the inner surface 42 being not coaxial with its outer surface 41 (see FIG. 16). As shown in FIG. 17, during the assembly of the shaft, the over-center ring 40 is slipped over the inner shaft tube 15 until it engages with an end section of the outer shaft tube 14. In the next step, a cover tube is shifted over the outer shaft tube 14 including the over-center ring 40 biasing its cylindrical outer surface 41 into a coaxial orientation (see FIG. 18). The cylindrical inner surface 42 is thus biased into a non-coaxial orientation. Thus, when the over-center ring 40 is forced with its outer surface 41 substantially in alignment with the outer surface of the outer shaft tube 14, the inner surface 42 of the over-center ring 40 engages frictionally with the inner shaft tube 15. If the outer and inner shaft tubes 14, 15 are made of steel with an inner shaft tube diameter of about 5 mm, for example, the over-center ring 40 may have a length of about 14 mm. In this way, the outer shaft tube 14 can be securely locked longitudinally to the inner shaft tube 15 at almost any longitudinal position. In FIG. 18, the cover tube is not shown. The over-center ring 40 may comprise a hole 43 for insertion of a tool for moving it. As shown in FIG. 16, the hole 41 may be designed for being engaged by an Allen key, for example.

Figure 19:
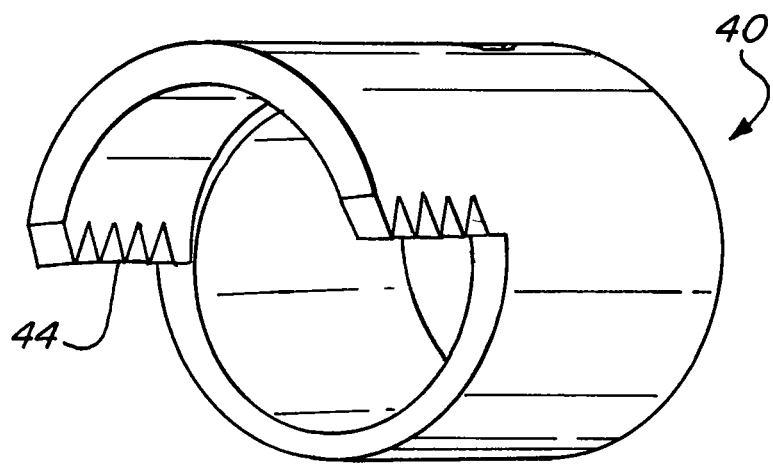
FIG. 19 shows a particular embodiment of the over-center ring.

As shown in FIG. 19, the connection between the over-center ring 40 and the outer shaft tube 14 can be improved by tooth means 44 engaging with corresponding indentations in the outer shaft tube (not shown).

In the first, second and third embodiments, the design of the actuation rod has not been described. However, the actuation rod preferably is telescopically adjustable and blockable by a similar mechanism as the shaft tube in the respective embodiment. In the third embodiment, in order to reduce the force to be exerted upon the over-center ring of the actuation rod for clamping, the over-center ring may comprise an extension in a longitudinal direction; moreover, a friction reducing material such as a suitable plastic material may be provided between the inner shaft tube and the actuation rod tube for reducing friction between the actuation rod and the shaft tube.

Figure 20:
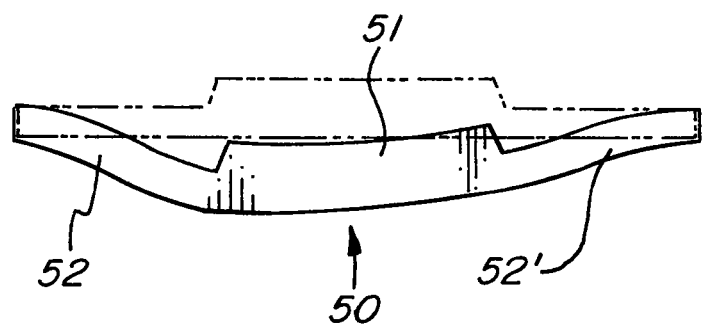
FIG. 20 shows a clamping element of an inner shaft tube according to a fourth embodiment of the invention in a sectional view.
Figure 21:
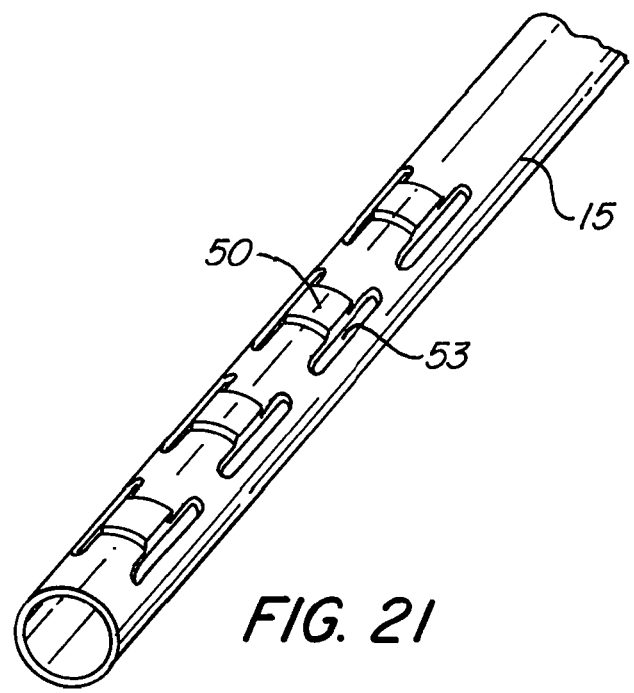
FIG. 21 shows an inner shaft tube according to the fourth embodiment with clamping elements according to FIG. 20.
Figure 22:
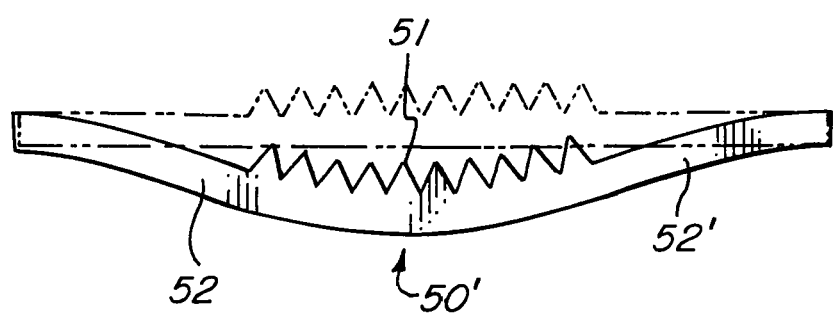
FIG. 22 shows an alternative embodiment of a clamping element.
Figure 23:
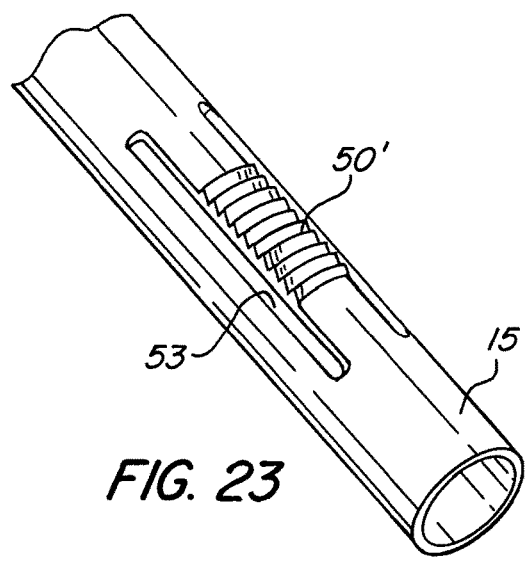
FIG. 23 shows an inner shaft tube according to the fourth embodiment with clamping elements according to FIG. 22.

According to a fourth embodiment, the inner shaft tube includes clamping elements 50, which comprise a central section 51 exhibiting an enlarged thickness as compared to the wall of the inner shaft tube, the clamping element 50 also comprising resilient connecting sections 52, 52' for connecting the clamping element 50 to the inner shaft tube wall. In FIG. 20, a clamping element 50 is shown in its deflected position (lower image) and in its straight position (upper image, thin lines). An inner shaft tube 15 comprising a multiplicity of clamping elements 50 is shown in FIG. 21, with the clamping elements 50 being in a straight position protruding beyond the outer surface of the inner shaft tube 15. An alternative embodiment of a clamping element 50' is shown in FIG. 22 in its deflected and in its straight position (lower and upper image, respectively), and an inner shaft tube 15 with such a clamping element 50' is shown in FIG. 23. In the alternative embodiment, the central section 51' exhibits a toothed structure for increased flexibility. The clamping elements 50, 50' may be formed by pressing the material of the inner shaft tube 15 and by laser cutting the lateral slits 53.

Figure 24:
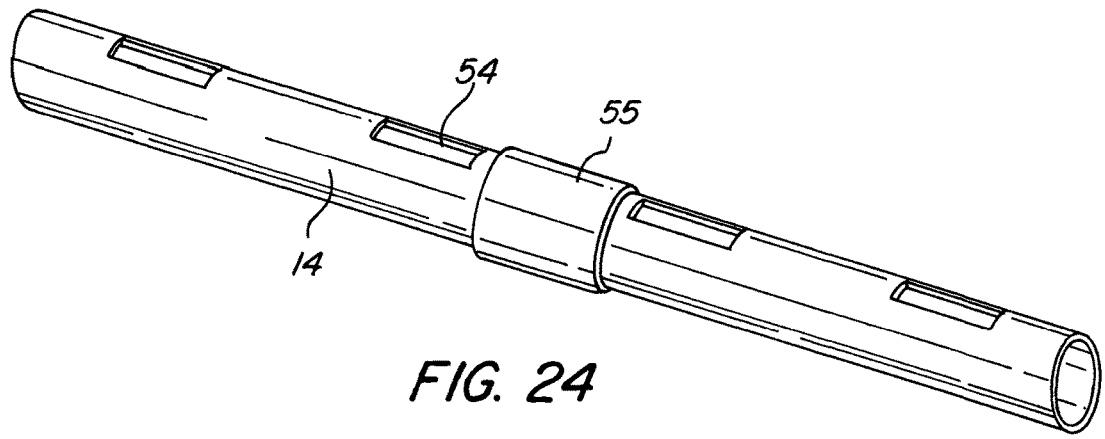
FIG. 24 shows an outer shaft tube according to the fourth embodiment.
Figure 25:
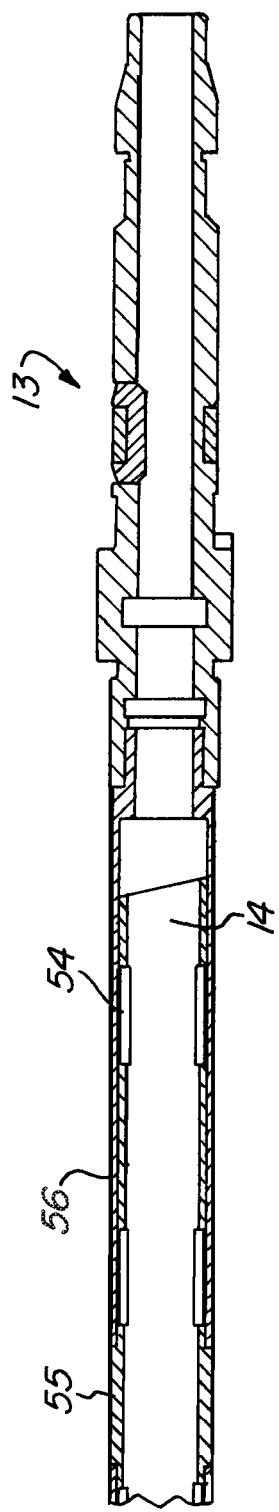
FIG. 25 shows the connection of the outer shaft tube of FIG. 24 to the coupling mechanism.

As depicted in FIG. 24, an outer shaft tube 14 comprises windows 54 for accommodating at least the central parts 51, 51' of the clamping elements 50. The outer shaft tube 14 is enclosed by a cover tube (not shown) which is segmented and held in place by a cover tube holding section 55 of the outer shaft tube 14. The outer shaft tube 14 is connected on its proximal end to the coupling mechanism 13 of the shaft to the handle, as shown in FIG. 25. The cover tube consists of segments 56. The cover tube may be enclosed by an outer sheath which has a smooth outer surface (not shown).

During assembly of the shaft the inner shaft tube 15 is inserted into the outer shaft tube 14 and moved in a longitudinal direction within the outer shaft tube 14. In this situation, the clamping elements 50, 50' are forced by the outer shaft tube 14 into their deflected positions. At a desired longitudinal position, the inner shaft tube 14 is turned so that the clamping elements 50, 50' coincide with the windows 54 of the outer shaft tube. The clamping elements 50, 50' resiliently latch into the windows 54, thus locking the inner shaft tube 14 with respect to the outer shaft tube 15. When the actuation rod is inserted into the inner shaft tube 14, the central sections 51 of the clamping elements 50, 50' will be held engaged with the windows 54 due to the increased thickness of the central sections 51 with respect to the inner shaft tube wall, the inner shaft tube 14 effectively being blocked with respect to the outer shaft tube 15. Due to the blocking effect of the actuation rod, the clamping elements 50, 50' need not necessarily be biased into their straight position, but may be forced by insertion of the actuation rod into the windows 54; however, assembly and adjustment are facilitated by latching of the clamping elements 50, 50' into the windows 54 due to a biasing force exerted by the connecting sections 52, 52'.

Figure 26:
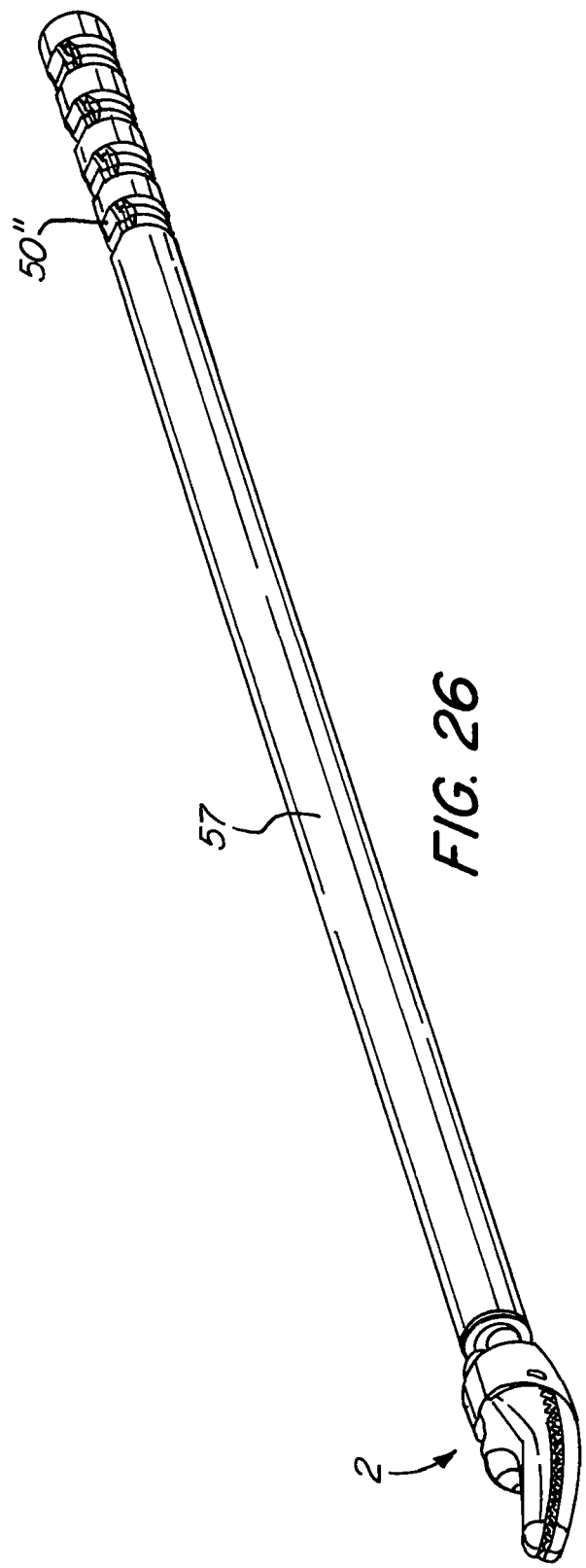
FIG. 26 shows the actuation rod tube according to the fourth embodiment in a perspective view.

An actuation rod according to the fourth embodiment is shown in FIGS. 26-28. An actuation rod tube 57 comprises one or a multiplicity of clamping elements 50'' designed as shown in FIG. 20 or 22, but protruding to the inside of the actuation rod tube 57 (see FIG. 26). At its distal end, the actuation rod tube 57 is connected to the surgical tool 4. An actuation rod core 58 comprises a multiplicity of recesses 59 or pockets for accommodating at least the central sections of the clamping elements 50'' (see FIG. 27). At its proximal end, the actuation rod core 58 is connectable to the handle. For this purpose, the actuation rod core 58 comprises a ball 20 to be engaged by a movable part of the handle and further recesses 60 for securing the connection to the handle (see below). As shown in the longitudinal sectional view of FIG. 28, after assembly and adjustment to a desired length, the actuation rod core 58 is locked within the actuation rod tube 56 by the clamping elements 50'' engaging with the recesses 59.

Figure 29:
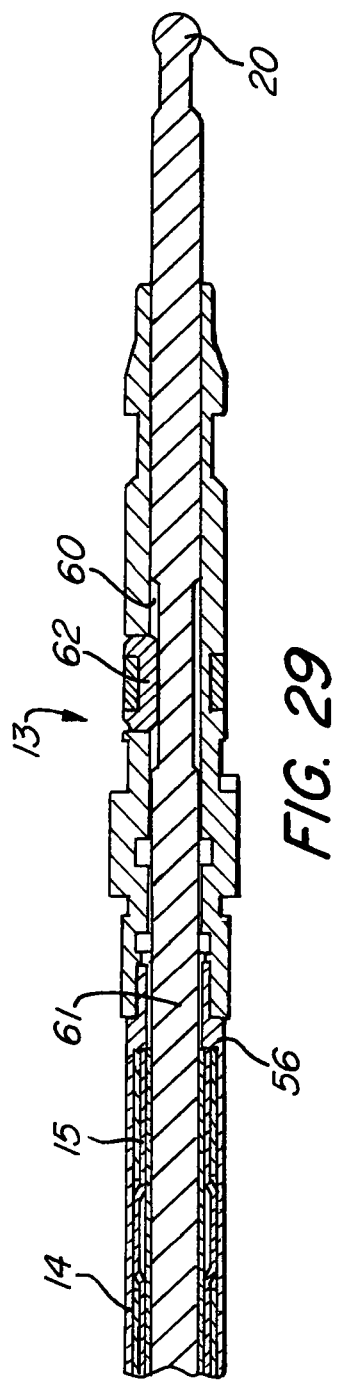
FIG. 29 shows the proximal end section of the actuation rod and the shaft tube and connected with the coupling mechanism in a longitudinal sectional view.

As shown in FIG. 29, the outer shaft tube 14 and cover tube segments 56 are connected to the coupling mechanism 13. The actuation rod 61, which is formed as a single rod in the section shown in FIG. 29, protrudes through the coupling mechanism 13, ending in a ball 20 and being held by a clamping element 62 engaging the recess 60 for sliding movement within a limited range. The shaft is formed by an inner shaft tube 15 comprising clamping elements 50 engaging with windows 54 of the outer shaft tube 14 (see FIG. 30). The outer shaft tube 14 also comprises cover tube holding sections 55 for fixing the cover tube sections 56 longitudinally. In the section shown in FIG. 30, the actuation rod 61 is formed as a single rod.

Figure 30:
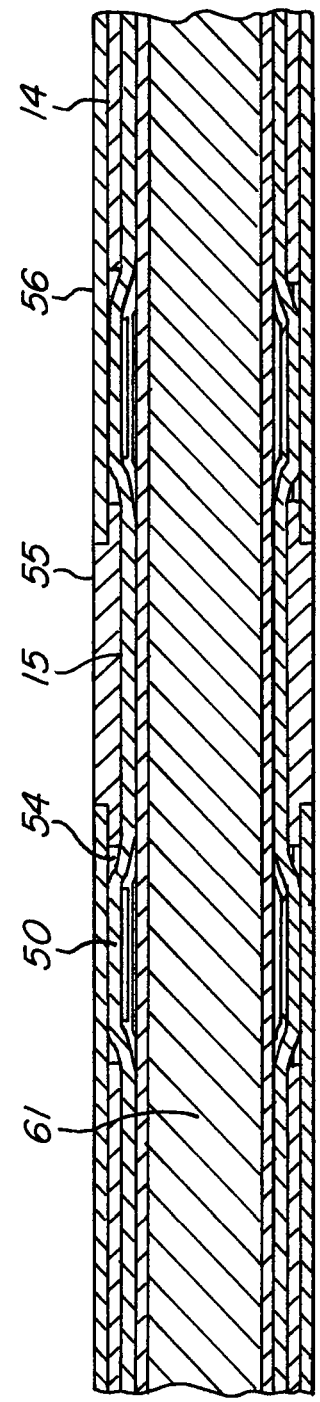
FIG. 30 shows the shaft in an assembled state in a longitudinal sectional view.
Figure 31:
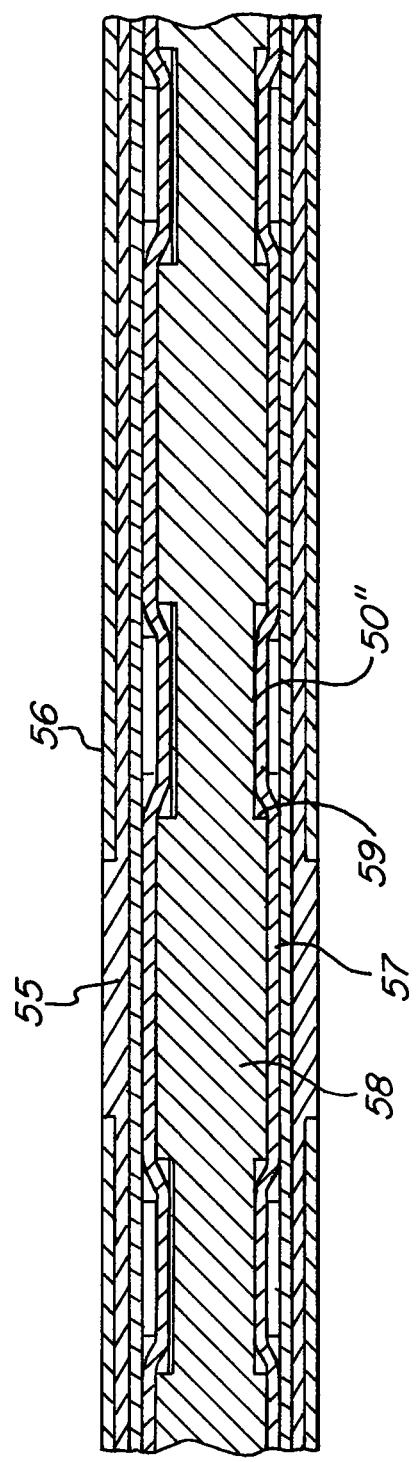
FIG. 31 shows the actuation rod in an assembled state in a longitudinal sectional view.

The actuation rod 61 in its assembled state comprises an actuation rod core 58 with recesses 59 engaged by clamping elements 50'' of an actuation rod tube 57 (see FIG. 31). In the section depicted in FIG. 31, the shaft is formed by the outer tube with cover tube holding section 55 and cover tube segments 56 only. In FIGS. 29-31, the clamping elements 50 are depicted without showing an increased thickness of their central sections.

The surgical instrument 1 described may have a minimal shaft length of 330 mm, 450 mm, or 600 mm, and be adjustable to a shaft length extended by up to 300 mm, for example.

What is claimed is:

1. A surgical instrument comprising:
   an elongate shaft;
   a surgical tool arranged at a distal end of the shaft for conducting surgical manipulations;
   a handle arranged at a proximal end of the shaft for actuating the surgical tool;
   the shaft having an elongate shaft tube and an elongate actuation rod arranged movably within the shaft tube;
   the tool and the handle both being connected to the shaft tube and the actuating rod such that the tool can be actuated by the handle through a motion of the actuating rod relative to the shaft tube;
   the shaft tube having an elongate outer shaft tube and an elongate inner shaft tube that is at least partly arranged within the outer shaft tube;
   wherein the outer shaft tube is displaceable in a longitudinal direction with respect to the inner shaft tube, a first locking mechanism which configures the outer shaft tube to be lockable against longitudinal displacement with respect to the inner shaft tube in a multiplicity of longitudinal positions, such that a length of the elongate shaft tube varies when the outer shaft tube is locked in each of the multiplicity of longitudinal positions;

the actuation rod having an elongate actuation rod tube and an elongate actuation rod core at least partly arranged within the actuation rod tube;

wherein the actuation rod tube is displaceable in a longitudinal direction relative to the actuation rod core, a second locking mechanism which configures the outer shaft tube to be lockable against longitudinal displacement with respect to the actuation rod core in a multiplicity of longitudinal positions, such that a length of the elongate actuation rod varies when the actuation rod tube is locked in each of the multiplicity of longitudinal positions:

wherein the first locking mechanism is a threaded bayonet-type lock.

2. The surgical instrument according to claim 1, wherein the second locking mechanism is a bayonet-type lock.

3. The surgical instrument according to claim 1, wherein the bayonet-type lock is blocked by at least one elongate blocking element.

4. The surgical instrument according to claim 1, wherein the second locking mechanism is defined by a proximal rod section of the actuation rod tube and a distal rod section of the actuation rod tube, the proximal rod section and the actuation rod core having a first ratchet permitting moving the proximal rod section in a distal direction over the actuation rod core and the distal rod section and the actuation rod core having a second ratchet permitting moving the distal rod section in a proximal direction over the actuation rod core, the first ratchet and the second ratchet each blocking movement in a respective opposite direction.

5. The surgical instrument according to claim 1, wherein the second locking mechanism comprises a clamping ring, the actuation rod tube connects to the clamping ring, the clamping ring having non-parallel cylindrical outer and inner surfaces such that the clamping ring frictionally engages with the actuation rod core when its outer surface is biased into a coaxial orientation by the inner shaft tube.

6. The surgical instrument according to claim 5, wherein the clamping ring is connected to the actuation rod tube by tooth means, respectively.

7. The surgical instrument according to claim 1, wherein the second locking mechanism is a clamping element and recess, the actuation rod tube defining the clamping element and the actuation rod core defining the recess for engaging with the clamping element.

8. The surgical instrument of claim 1, wherein the first locking mechanism is disposed on the outer shaft tube between a distal end of the handle and a proximal end of the tool for locking the outer shaft tube to the inner shaft tube.

9. A surgical instrument comprising:
a shaft having a tube,
the tube having an outer tube and an inner tube that is at least partly arranged within the outer tube, and an actuation rod arranged movably within the tube,
the actuation rod having an actuation rod tube and an actuation rod core at least partly arranged within the actuation rod tube;
a first locking mechanism which configures the outer tube to be lockable relative to the inner tube in a first position and a second position, wherein in the first position, the tube is a first length, and in the second position, the tube is a second length different than the first length;
a second locking mechanism which configures the actuation rod tube to be lockable relative to the actuation rod core in a third position and a fourth position, wherein in the third position, the actuation rod is a third length, and in the fourth position, the actuation rod is a fourth length different than the third length;
wherein the first locking mechanism is defined by a proximal section of the outer shaft tube and a distal shaft section of the outer shaft tube, the inner shaft tube having a first ratchet permitting moving the proximal shaft section in a distal direction over the inner shaft tube and the distal shaft section and the inner shaft tube having a second ratchet permitting moving the distal shaft section in a proximal direction over the inner shaft tube, the first and the second ratchet each blocking movement in a respective opposite direction.

10. The surgical instrument according to claim 9, wherein the outer and inner shaft tubes and/or the actuation rod tube and the actuation rod core, respectively, are rotatable with respect to each other for releasing the first ratchet.

11. The surgical instrument according to claim 10, wherein the rotation of the outer and inner shaft tubes is blocked by a cover tube and/or the rotation of the actuation rod tube and the actuation rod core relative to each other is blocked by the inner shaft tube, respectively.

12. The surgical instrument according to claim 9, wherein the second locking mechanism is a bayonet-type lock.

13. The surgical instrument according to claim 9, wherein the second locking mechanism is defined by a proximal rod section of the actuation rod tube and a distal rod section of the actuation rod tube, the proximal rod section and the actuation rod core having a first ratchet permitting moving the proximal rod section in a distal direction over the actuation rod core and the distal rod section and the actuation rod core having a second ratchet permitting moving the distal rod section in a proximal direction over the actuation rod core, the first ratchet and the second ratchet each blocking movement in a respective opposite direction.

14. The surgical instrument according to claim 9, wherein the second locking mechanism comprises a clamping ring, the actuation rod tube connects to the clamping ring, the clamping ring having non-parallel cylindrical outer and inner surfaces such that the clamping ring frictionally engages with the actuation rod core when its outer surface is biased into a coaxial orientation by the inner shaft tube.

15. The surgical instrument according to claim 9, wherein the second locking mechanism is a clamping element and recess, the actuation rod tube defining the clamping element and the actuation rod core defining the recess for engaging with the clamping element.

16. A surgical instrument comprising:
an elongate shaft;
a surgical tool arranged at a distal end of the shaft for conducting surgical manipulations;
a handle arranged at a proximal end of the shaft for actuating the surgical tool;
the shaft having an elongate shaft tube and an elongate actuation rod arranged movably within the shaft tube;
the tool and the handle both being connected to the shaft tube and the actuating rod such that the tool can be actuated by the handle through a motion of the actuating rod relative to the shaft tube;
the shaft tube having an elongate outer shaft tube and an elongate inner shaft tube that is at least partly arranged within the outer shaft tube;
wherein the outer shaft tube is displaceable in a longitudinal direction with respect to the inner shaft tube, a first locking mechanism which configures the outer shaft tube to be lockable against longitudinal displacement with respect to the inner shaft tube in a multiplicity of longitudinal positions, such that a length of the elongate shaft tube varies when the outer shaft tube is locked in each of the multiplicity of longitudinal positions;

the actuation rod having an elongate actuation rod tube and an elongate actuation rod core at least partly arranged within the actuation rod tube;

wherein the actuation rod tube is displaceable in a longitudinal direction relative to the actuation rod core, a second locking mechanism which configures the outer shaft tube to be lockable against longitudinal displacement with respect to the actuation rod core in a multiplicity of longitudinal positions, such that a length of the elongate actuation rod varies when the actuation rod tube is locked in each of the multiplicity of longitudinal positions;

wherein the first locking mechanism is a clamping element and a window or recess, the outer shaft tube defining the clamping element and the inner shaft tube defining the window or recess for engaging with the clamping element wherein the clamping element engaging with a window or recess is blocked by a cover tube enclosing the outer shaft tube and/or the clamping element engaging with a recess is blocked by the actuation rod tube, respectively.

17. The surgical instrument according to claim 16, wherein the second locking mechanism is a bayonet-type lock.

18. The surgical instrument according to claim 16, wherein the second locking mechanism is defined by a proximal rod section of the actuation rod tube and a distal rod section of the actuation rod tube, the proximal rod section and the actuation rod core having a first ratchet permitting moving the proximal rod section in a distal direction over the actuation rod core and the distal rod section and the actuation rod core having a second ratchet permitting moving the distal rod section in a proximal direction over the actuation rod core, the first ratchet and the second ratchet each blocking movement in a respective opposite direction.

19. The surgical instrument according to claim 16, wherein the second locking mechanism comprises a clamping ring, the actuation rod tube connects to the clamping ring, the clamping ring having non-parallel cylindrical outer and inner surfaces such that the clamping ring frictionally engages with the actuation rod core when its outer surface is biased into a coaxial orientation by the inner shaft tube.

20. The surgical instrument according to claim 16, wherein the second locking mechanism is a clamping element and recess, the actuation rod tube defining the clamping element and the actuation rod core defining the recess for engaging with the clamping element.

* * * * *